(12) United States Patent
Tabasso

(10) Patent No.: US 6,514,509 B2
(45) Date of Patent: *Feb. 4, 2003

US006514509B2

(54) METHOD FOR PRODUCTION ON THE SPOT OF A DISINFECTANT PERACETIC ACID SYSTEM

(75) Inventor: Renato Tabasso, San Remo (IT)

(73) Assignee: Farmec S.n.c. di Tabasso Renato & C., Settino di Pescantina (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/296,169

(22) Filed: Apr. 22, 1999

(65) Prior Publication Data

US 2002/0004057 A1 Jan. 10, 2002

(30) Foreign Application Priority Data

Apr. 30, 1998 (IT) .......................... VR98A0033

(51) Int. Cl.⁷ ...................... A01N 25/00; A61K 31/075; A61L 9/00
(52) U.S. Cl. ...................... 424/405; 514/714; 422/28; 422/29
(58) Field of Search .......... 424/405; 514/714; 422/28, 29

(56) References Cited

U.S. PATENT DOCUMENTS

| 3,227,655 | A | * | 1/1966 | Prett et al. ............. 252/186.23 |
| 4,051,058 | A | | 9/1977 | Bowing et al. |
| 4,103,001 | A | | 7/1978 | Schattner |
| 4,900,721 | A | * | 2/1990 | Bansemir et al. ............. 424/49 |
| 5,116,575 | A | * | 5/1992 | Badertscher et al. .......... 422/28 |
| 5,279,735 | A | | 1/1994 | Cosentino et al. |
| 5,350,563 | A | * | 9/1994 | Kralovic et al. .............. 422/28 |

FOREIGN PATENT DOCUMENTS

| DD | 286370 | 1/1991 |
| DE | 3638552 | 5/1988 |
| DE | 3743224 | 6/1989 |
| EP | 0125781 | 11/1984 |
| EP | 0361955 | 4/1990 |
| WO | 94 18297 | 8/1994 |
| WO | 96 18297 | 6/1996 |

OTHER PUBLICATIONS

CA abstract, AN: 1996:597822, Croud et al., 1996.*
S.S. Block "Disinfection, Sterilization and Preservation" 1992, Lea & Febiger, Philadelphia, US XP002112246.
"Sterilants and High Level Disinfectants cleared by FDA in a 510(k) as of Oct. 1, 1998 with General Claims for Processing Reusable Medical and Dental Devices".
"Peract 20™ Liquid Cold Sterilant/Disinfectant" UNITROL Division of Minntech Corporation.

* cited by examiner

Primary Examiner—Russell Travers
Assistant Examiner—Shengjun Wang
(74) Attorney, Agent, or Firm—Guido Modiano; Albert Josif; Daniel O'Byrne

(57) ABSTRACT

A method for preparing a disinfectant and sterilizing peracetic acid solution, comprising the production just before use of peracetic acid by mixing an activator (HP) with a parent mixture.

6 Claims, No Drawings

METHOD FOR PRODUCTION ON THE SPOT OF A DISINFECTANT PERACETIC ACID SYSTEM

This application claims foreign priority of Italy VR98A000033, filed Apr. 30, 1998.

BACKGROUND OF THE INVENTION

The present invention relates to a method for production on the spot of a peracetic acid (PAA) aqueous solution (disinfectant system) used for high-level chemical disinfection and chemical cold-sterilization of many devices, equipment and plants, e.g.
- medical and surgical devices, including fiber-optic instruments (endoscopes, etc.), bed sheets or other fabrics used in the sanitary field (hospitals, surgeries, etc.);
- tools, surfaces, instruments, CIP (cleaning in place) pipes, and objects in general in the field of food handling;
- wastewater treatment plants;
- and in any other field requiring a high-level disinfection or chemical cold-sterilization treatment.

Efficient sterilization methods are required for industrial and sanitary applications. For their repeated use, various tools and devices require safe, effective and fast disinfection and sterilization procedures. Although most "critical" multiple-use medical-surgical instruments are sterilized, after accurate cleaning, by:
- dry heat treatment,
- wet heat treatment (steam autoclave),
- ethylene oxide sterilization (for plastics), there are, however, devices (for example endoscopes, etc.), especially in the sanitary field, which are made of highly heat-sensitive material and thus cannot be subjected to the above treatments.

Moreover, since some of such devices are often used for diagnostic and therapeutic purposes in daily activity, their passage through ethylene oxide autoclaves, although being feasible, is impractical owing to both excessively high costs and time limits. Accordingly, high-level disinfection and sterilization with chemical products at room temperature is the only feasable procedure for such instruments.

Many "cold-sterilizing" compositions have been suggested so far, e.g. 2%, 2.5%, 3.2% glutaraldehyde, buffered to pH 7.5–8.5 upon being used, and the phenol-phenate buffer system in association with glutaraldehyde (Sporicidin™) or, more recently, "Sporicidin Plus™", an association of phenol, phenolic derivatives and glutaraldehyde; see U.S. Pat. No. 4,103,001 (Schattner). All these products have in common the presence of glutaraldehyde and make it possible to obtain sterilization of the devices, but only after extremely long contact times.

A process or a product can be considered to be a sterilizer only if it can eliminate all microbial life forms, including spores, which have the highest resistance to sterilization processes. Accordingly, a sterilizing chemical preparation must be bactericidal, fungicidal, virucidal and sporicidal.

A relatively small number of antimicrobial agents is actually sporicidal and thus usable as "chemosterilizers". One of them is peracetic acid, a peroxide agent, which has a wide and rapid germicidal activity. The FDA (Food and Drug Administration) has long recognized as 510 (k)-cleared chemical sterilization agents two products whose active principle is peracetic acid:
- Steris 20™ (0.2% peracetic acid at 50–56° C. for 12 minutes of contact)
- Peract 20™ (0.08% peracetic acid plus 1% hydrogen peroxide at 20° C. for 8 hours of contact).

The first product is a concentrated solution of 35% w/w peracetic acid, which has a six-month stability period. The second product is a ready-for-use acid aqueous solution, which has a stability period of one year.

Peracetic acid has the same attributes as hydrogen peroxide (germicidal and sterilizing capacities, non-dangerous decomposition products and infinite solubility in water), but is more soluble in lipids and insensitive to deactivation by catalase and peroxidase enzymes. It is also a more powerful antimicrobial agent than hydrogen peroxide, since it is rapidly active at low concentrations against a broad range of microorganisms. Furthermore, it is sporicidal at very low temperatures and remains effective even in the presence of organic material. As a weak acid it is more active in an acid environment.

Aqueous solutions of concentrated peracetic acid and hydrogen peroxide have already been proposed commercially; however, they have a very short stability period. A certain stability is ensured by the presence of an excess of acetic acid and/or hydrogen peroxide with respect to the equilibrium for solutions of peracetic acid ranging from 0.5% to 50% w/w. Moreover, the addition of a sequestrant for metallic ions to the aqueous solution, e.g. a diphosphonic acid and an anionic surfactant belonging to the class of alkylbenzene sulfonates, alkylsulfonates or alkane sulfonates, as disclosed in U.S. Pat. No. 4,051,058 (Bowing et al.), ensures further stability of the concentrated peracetic-acid aqueous solutions used to prepare diluted microbicidal solutions in a sanitary and food-handling environment. However, these concentrated solutions, when correctly preserved, can be considered as stable for up to six months without appreciable losses of active oxygen.

The "six month" term is highly penalizing from the commercial point of view, especially because it does not allow storage on an industrial scale (that is to say, storage in relevant amounts), and this has a negative effect on the final cost of peracetic acid (PAA).

In general, peroxides are high energy state compounds and as such can be considered to be thermodynamically unstable. Peracetic acid (PAA) is much less stable than hydrogen peroxide (HP). A 40% w/w solution of PAA loses 1 to 2% of its active ingredient per month, compared with hydrogen peroxide (30 to 90%), which loses less than 1% per year. The decomposition products of peracetic acid are acetic acid, hydrogen peroxide (HP), oxygen and water. Dilute solutions of peracetic acid are even less stable. Thus, for example, a 1% solution loses half of its concentration by hydrolysis in six days.

After succeeding in producing highly concentrated hydrogen peroxide, peracetic acid has been produced on an industrial scale by the reaction of acetic acid or acetic anhydride with concentrated hydrogen peroxide in the presence of sulfuric acid, which acts as a catalyst, as shown by the following reaction formula:

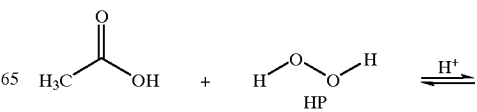

-continued

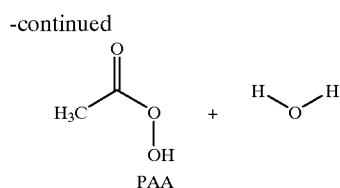
PAA

In order to prevent the inverse reaction, peracetic acid solutions are boosted with acetic acid and hydrogen peroxide (HP). Moreover, a stabilizing agent is used, e.g. a sequestrant (sodium pyrophosphate) or a chelating agent (8-hydroxyquinoline) to remove any trace of metallic ions, which would accelerate the decomposition of peroxides. A system in which use is made of anionic surfactants in PAA solutions has not only higher stability but also a higher antimicrobial activity—see U.S. Pat. No. 4,051,058. Finally, synergistic effects between PAA and ethyl alcohol or isopropyl alcohol have been noted in connection with germicidal activity.

Despite the various proposals as described above, when stable commercial peracetic acid is diluted with water it decomposes rapidly. Such a decomposition can be accelerated by high temperatures and the presence of heavy metals in the solution. Accordingly, it is advisable to dilute the peracetic acid with deionized or distilled water, store it in a cool place and use it as soon as possible. The decomposition of peracetic acid can occur in the three following manners:

Oxygen is formed in reaction (1). The rate of decomposition in this way depends on the nature and quantity of heavy metals in the solution. This reaction is often responsible for the loss of activity of insufficiently stabilized PAA solutions.

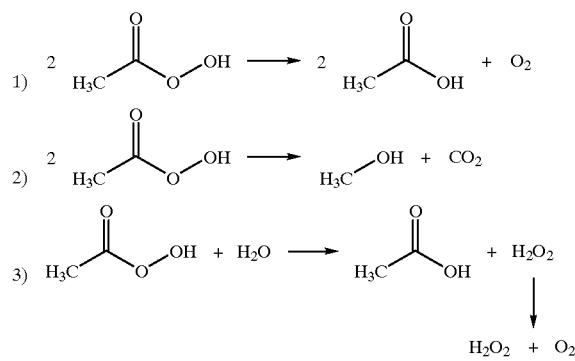

Reaction (2) proceeds via intermediate radicals. Methyl radicals may be formed among other substances. Similarly to reaction (1), also this reaction is catalyzed by metallic ions.

The hydrolysis of peracetic acid (reaction 3) is highly pH-dependent. It takes place whenever peracetic acid solutions are diluted. The reaction products are acetic acid and hydrogen peroxide.

Every dilution of commercially available PAA solutions results in a new equilibrium being reached between peracetic acid, acetic acid, hydrogen peroxide and water. Although it is possible to dilute solutions of peracetic acid, the concentration obtained upon dilution may change later because the equilibrium can shift.

Peracetic acid is reactive in any concentration and can only be stored for long periods if adequately stabilized. In controlled storage conditions and at room temperature the loss of activity is very small. Peracetic acid has a high oxidation potential and is highly reactive. As the pH increases, its stability decreases. When it is put contact with sodium hydroxide or other alkaline media, decomposition occurs. Ions of heavy metals, e.g. copper, manganese and iron, start catalytic decomposition. Heat and contact with incompatible solutions might give rise to decomposition process.

SUMMARY OF THE INVENTION

The main object of the present invention is to provide a simple system for preparing on demand a sterilizing aqueous solution based on peracetic acid and other additives that enhance its germicidal properties with a synergistic effect. Since this system generates peracetic acid only upon being used, it not affected by stability and storage problems as mentioned above, which are due to its active principle and faced with all commercially available aqueous solutions of various concentrations of peracetic acid.

DETAILED DESCRIPTION OF THE INVENTION

This and other objects which will become better apparent hereinafter are achieved, according to the invention, by a two-component system which comprises a main parent solution and an activator to be added to the parent solution immediately before use to form peracetic acid by simple equilibrium.

Advantageously, to ensure higher stability, germicidal activity and compatibility with the treated materials, preparation on the spot before use is made at room temperature and the solution can be buffered to a pH ranging from 3.5 to 7.0 at 20° C. Moreover, such a system according to the invention is a new solution of peracetic acid, which differs from commercially available solutions since it has, at equilibrium, a variable excess of one of the two reagents to avoid hydrolysis phenomena which affect the active principle. As a matter of fact, concentrated peracetic acid solutions available on the market have a very specific concentration of hydrogen peroxide and acetic acid in excess with respect to the equilibrium. Thus, regardless of the dilution, molar ratios among the various components remain always the same.

According to the present invention, since concentration of the acetylated compound (acetic acid or tetraacetyl glycoluryl) in the parent solution and concentration of the peroxide in the activator can vary independently from one another, it is possible to obtain a wide variety of concentrations in excess with respect to equilibrium of one or both reactive components in the activated solution.

Furthermore, concentrations of peracetic acid that can be obtained from the preparation according to the present invention can vary between 0.01% and 10.00% w/w. With this concentration range, it is possible to achieve a wide range of ready-for-use solutions and of concentrated solutions to be diluted in water, having a high bactericidal, fungicide, virucidal, tubercolicidal and sporicidal activity for extremely short contact times.

A. The parent solution has the following composition:

| | | |
|---|---|---|
| a) | N-acetylated compounds (e.g. N, N', N", N'''-tetracetylglycoluryle (TAGU), tetracetyl ethylene diamine (TAED) | 0.001–13.000% w/w |

| | | |
|---|---|---|
| b) | O-acetylated compounds (e.g. glacial or concentrated acetic acid) | 0.001–81.000% w/w |
| c) | Deionized water: remainder up to | 100.000% w/w | and optionally at least one of the following components:
1. An acetate salt, in a variable amount depending upon the % of acetic acid in order to form the buffer system for buffering the pH to 3.50–7.00 at 20° C.;
2. Other buffer systems suitable for buffering the pH of the parent solution and the activated solution at between 3.5 and 7.0 at 20° C. (e.g. sodium carbonate, sodium bicarbonate, monosodium phosphate, sodium hydroxide; weak monocarboxylic and polycarboxylic organic acids such as citric acid, tartaric acid or the like);
3. A oxide reduction indicator (such as amaranth red) as necessary (traces)

| | | |
|---|---|---|
| 4. | Primary, secondary and tertiary long- and short-chain alcohols (e.g. ethyl alcohol and isopropyl alcohol) | 0.001–35.000% w/w; |
| 5. | Stabilizing agents (sequestrant or chelating agents for metallic ions, e.g. diphosphonic acids, ethylenediaminotetraacetic acid (EDTA)), sodium pyrophosphate, 8-hydroxyquinoline) | 0.001–15.000% w/w; |
| 6. | Anionic surfactants, such as sulfates and sulfonates (e.g. sodium alkyl ($C_6$–$C_{18}$) benzene sulfonate) | 0.001–5.000% w/w; |
| 7. | A wetting agent (e.g. glycerine, propylene glycol) | 0.001–10.000% w/w; |
| 8. | A strong inorganic acid (concentrated sulfuric acid) | 0.001–1.000% w/w. |

Essential and indispensable reactive components of the parent solution are O-acetylated compounds, such as glacial acetic acid, and N-acetylated compounds, such as tetracetyl glycoluryle (TAGU) or tetraacetyl ethylene diamine (TAED).
B. The activator comprises a single component, i.e. a peroxide compound, such as potassium peroxydisulfate, peroxymonosulfate, peroxydisulphonic acid, hydrogen peroxide and derivatives thereof, e.g. potassium and sodium perborates, carbamide peroxide (also known as urea hydrogen peroxide), all of them in any physical state (solid, liquid and vapor) and at different concentrations of active oxygen. The amount of activator to be added to the parent solution can vary according to the desired concentration of peracetic acid and the molar excess of hydrogen peroxide with respect at equilibrium with respect to the other reagent (N- or O-acetylate derivative).

The present invention provides for a two-component system for preparation on the spot of a sterilizing aqueous peracetic acid solution and other additives which enhance its stability and germicidal activity as well as compatibility with various materials. These solutions can be concentrated and therefore intended for dilution with water just before use, or can be solutions ready for use. They can have an acid pH or a buffered pH in the range of 3.50 to 7.00 at 20° C. for obtaining better compatibility with the materials. The two components are stored separately in two separate packages and combined only immediately before use. Peracetic acid forms only upon combination through chemical-physical equilibrium. In this manner, any problem related to the instability of peracetic acid and therefore to its extended storage are eliminated, since active principle forms only after combining two separately stored components.

This system makes also possible to obtain a solution which has markedly better germicidal, stability and materials-compatibility characteristics than conventional aqueous solutions based on PAA—see the following

| Characteristic | PAA aqueous solution | Two-component system according to the present invention |
|---|---|---|
| Germicidal activity | Only due to the PAA | Owing to the synergistic effect of an alcohol, of an anionic surfactant and of the hydrogen peroxide in excess with respect to the equilibrium, the concentration of PAA being equal, the solution has a better germicidal activity |
| Stability and shelf life | No more than six months for concentrated solutions | 2 years (since the stability of the entire system depends on the stability of the activator, not on the peracetic acid (PAA)) |
| Materials compatibility | Highly acid pH which contributes to oxidation and therefore corrosion of sensitive materials | The pH of the activated solution is buffered to acid-neutral values (3.5–7.0 at 20° C.) which have a positive effect on the materials with which the solution is brought into contact. |

For a better understanding of the innovative characteristics according to the present invention one should consider the function of each component.

A. Parent solution a) N-acetylated compounds (tetracetyl glycoluryle (TAGU) or tetracetyl ethylene diamine (TAED): this is the essential reagent for the preparation of PAA by reaction with peroxide activator (see formula 4). It has the same function as acetic acid. However, with respect to acetic acid it reacts more quickly with hydrogen peroxide. In terms of reaction kinetics, one could say that tetraacetyl glycoluryle is more electrophilic than acetic acid. Said N-acetylated derivative, therefore, allows peracetic acid to be rapidly formed when the parent solution is combined with activator. This reaction does not even require a catalyst. It is in fact known that nucleophilic attack of carbonyl carbon occurs more quickly for an imide (such as tetraacetyl glycoluryle) and an amide than for an acid or an ester. Chlorides of acids and anhydrides are even more electrophilic, but due to their high reactivity and instability in an aqueous solution they cannot be used for this purpose.

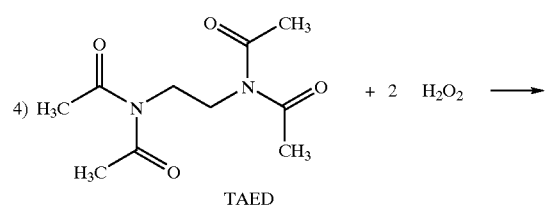

TAED

-continued

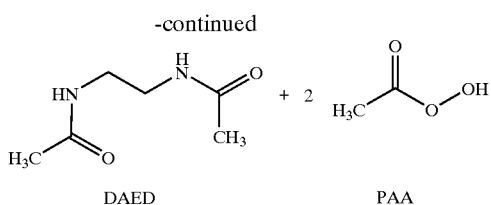

DAED    PAA b) Acetic acid has the same function as tetraacetyl glycoluryle, the only difference being that its reaction kinetics with hydrogen peroxide, other conditions being equal, is slower.

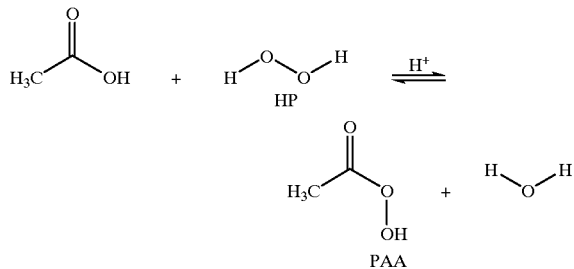

PAA

Accordingly, within the formulation the presence of tetraacetyl glycoluryle and of acetic acid allows immediate and prolonged formation of peracetic acid (PAA) as a consequence of activation. By varying their concentration, both the concentration at equilibrium of PAA and the reaction kinetics change. In other words, both the percentage w/w of peracetic acid and the waiting period after activation vary to obtain a preset concentration of PAA and the duration of the solution.

c) Acetated salts, e.g. sodium acetate, are the conjugate salts of a weak acid. Accordingly, together with the acid a buffer system is formed which buffers the pH of the solution to a value close to its own value of pKa, which is 4.75 in this case. Buffering the solution to these values of pH is a further innovation with respect to conventional solutions of PAA, which are highly acid. As a matter of fact, this makes it possible to use the solution also to sterilize particularly delicate instruments, such as fiber-optic instruments, without the risk of causing corrosive effects, which are much more frequent with highly acid solutions.

d) As a buffer system, it is possible to use all weak organic acids, as specified above, and the corresponding conjugate salts, or any strong base which allows an acetic acid/acetate salt buffer system to be generated. There are in fact two ways for buffering the pH:
  by adding, simultaneously with the solution to be buffered, a weak acid and, in a stoichiometric quantity, the corresponding conjugate salt;
  by adding only a weak acid and a strong base which is capable of converting part of the acid into its conjugate base or, vice versa, by adding the conjugate salt and a strong acid in order to convert part of the salt into the corresponding conjugate weak acid.

e) The oxyde-reduction indicator is designed to indicate to the operator that the parent solution has been activated. This is a compound which has a different color in the reduced state and in the oxidized state. By adding the activator, the oxidation state of the solution environment varies and accordingly the solution acquires a different color.

f) The primary, secondary and tertiary alcohols that can be used are short-chain alcohols, such as ethyl alcohol, n-propyl alcohol, isopropyl alcohol, butyl alcohol, or medium/long-chain alcohols, such as undecyl alcohol and the like, alkyl or arylalkyl alcohols having a germicidal activity. Of course, the alcohols that can be used in the composition according to the present invention must have a more or less significant miscibility with water to be able to mix uniformly with water without producing phase separation or a more or less stable emulsion. The presence of such an element constitutes an innovation with respect to all other disinfectant solutions based on PAA that are currently commercially available. The alcohol, in addition to acting as a preservative for the parent solution, in fact, also has a germicidal synergistic effect with the PAA.

g) The stabilizing agents are sequestrants or chelating agents (ethylenediaminotetraacetic acid (EDTA) and salts thereof, sodium tripolyphosphate, sodium pyrophosphate), which are designed to remove the traces of metallic ions, which would accelerate the decomposition of the peroxides. This category of stabilizing agents also includes the phosphonic acids disclosed in U.S. Pat. No. 4,051,058. However, preference is given to phosphonic acids having a low relative molecular mass and containing at least two anionic groups, one of which is a phosphonic acid group. These also include diphosphonic acids having the following formula:

where $R_1$ is a member chosen from the group that contains phenyl, cycloalkyl having 5 to 6 carbon atoms and alkyl having 1 to 6 carbon atoms, $R_2$ and $R_3$ are members chosen from the group comprising hydrogen, alkyls having 1 to 4 carbon atoms and amino alkyls having 1 to 4 carbon atoms. These include:
  aminotri(methylene phosphonic acid)
  dimethylaminomethane diphosphonic acid
  aminoacetic acid N-di-(methylene phosphonic acid)
  ethylene diamine tetra-(methylene phosphonic acid)
  1-amino-1-cyclohexylmethane-1,1-diphosphonic acid
  3-aminopropane-1-hydroxy-1,1-diphosphonic acid
  2-phosphone butane-1,2,4-tricarboxylic acid
  phosphone succinic acid
  1-phospone-1-methylsuccinic acid
  The following are particularly preferable:
  dimethylamine methane diphosphonic acid
  1-amino-1-phenyl methane diphosphonic acid
  amino-tri-(methylene phosphonic acid)
  aminoacetic acid N-di-(methylene phosphonic acid)
  1-hydroxyethane-1,1-diphosphonic acid
  These acids can also be used in the form of their water-soluble salts, particularly as alkaline metals, such as sodium and potassium. If required, it is also possible to use mixtures of individual phosphonic acids or of acid salts thereof.

h) The presence of at least one anionic surfactant ensures not only higher stability but also higher antimicrobial activity of the diluted solutions of PAA, as disclosed in U.S. Pat. No. 4,051,058. The anionic surfactants that can be used in the composition according to the present invention are of sulfate and sulfonate type, such as alkylbenzene sulfonates having 6 to 18 carbon atoms in the alkyl, alkyl sulfates and/or alkane sulfates (each having 8 to 22 carbon atoms in the alkyl or alkane group), added in amounts between 0.001 and 5% w/w.

The alkyl benzene sulfonates that can be used are preferably those containing an alkyl radical with 6 to 18 carbon atoms, preferably 9 to 15 carbon atoms. Instead of alkyl benzene sulfonates, it is possible to use alkyl sulfates or alkane sulfates with an alkyl or alkane radical having a chain of 12–18 carbon atoms. If required, it is of course possible to use mixtures of the above mentioned anionic surfactant compounds disclosed in U.S. Pat. No. 4,051,058.

i) The wetting agents that can be used belong to the category of polyols, such as propylene glycol, diethylene glycol and glycerine. All these compounds can be mixed with water and are designed to protect the objects to be disinfected from any aggressiveness of the product.

j) The strong inorganic acid acts as a catalyst for the reaction for preparing PAA, reducing the activation energy, i. e. providing a faster reaction. Like all the catalysts, the inorganic acid does not take part to the reaction and thus a few traces in the solution are sufficient. Among strong inorganic acids, preference is given to the use of concentrated sulfuric acid, as it is also used for the same purposes in industrial chemical production of concentrated solutions of peracetic acid. Besides being a strong acid, it is also an oxidizing and dehydrating agent. In this case, however, addition of inorganic acid affects only the rate of formation of the peracetic acid.

k) Purified water constitutes the solvent of the parent solution. The presence of this component is also an innovation, especially with respect to concentrated solutions based on PAA to be diluted at the time of use. The use of tape water for dilution in fact very often compromises the solution stability due to the presence of metallic ions which assist degradation of the peroxides.

B. Activator

The activator is a peroxide compound which releases active oxygen in water. All peroxide compounds share the active function $R_1$—O—O—$R_2$, which is responsible for the nucleophilic attack of the carbonyl carbon of the acetyl substrates. More particularly, concentrated hydrogen peroxide or derivatives thereof are used in any physical form and in any concentration. $H_2O_2$ (hydrogen peroxide) is the reagent involved in the formation equilibrium of the peracetic acid (PAA). It can be used in the form of an acid solution or as a salt, such as sodium perborate, carbamide peroxide which are instead basic in an aqueous solution.

Activation consists in combining the parent solution with the activator. After a waiting period in the range of between 30 minutes and 48 hours depending on the specific case, PAA concentrations are obtained which have broad-spectrum and swift microbicidal effects. These concentrations and activities remain stable for at least 5 days, if the activated solutions are stored at room temperature and are not subjected to intense shaking. Stability can be extended further if the solution is stored after use in a closed container away from heat and light sources.

Some currently preferred examples of preparation of a "chemosterilizing" solution according to the present invention are given hereinafter.

EXAMPLE 1

A parent solution having the following composition was prepared:

| Component | % w/w | g per 250 g of solution |
|---|---|---|
| Deionized water | 71 | 177.5 |
| Concentrated sulfuric acid (96%) | 1 | 2.5 |
| Glacial acetic acid | 28 | 70 |

The following instruments were used for this preparation:
a 300-ml flat-bottomed flask,
an Are 2 Velp Scientifica magnetic agitator,
a Mettler PM100 analytical balance (for weights up to 100 g)
a Mettler Toledo PB1502 technical balance (for weights of 100 to 1500 g).

The above listed components were weighed separately, taking particular care with the concentrated sulfuric acid, which must be handled under a hood and with protection gloves. The components were mixed in the above listed sequence, making sure that the component being dealt with was perfectly mixed before adding the next one. After addition of the components, the mixture was stirred for 15 minutes, left to rest for 10 minutes and a sample was retrieved for checking its chemical and physical properties.

All operations were performed at room temperature (20° C.), avoiding overheating the solution. When the concentrated sulfuric acid was added to the water, slight heating occurred, which was rapidly absorbed by the aqueous diluent.

The following chemical-physical properties were measured:

| Property | Unit of measure | Values |
|---|---|---|
| Specific gravity at 20° C. | g/ml | 1.028 ± 0.010 |
| pH (10% w/w in deionized water) at 20° C. | U of pH | 1.00–2.00 |
| Miscibility in water | | full |
| Appearance | | clear |
| Color | | colorless |

35% w/w of hydrogen peroxide was used as activator. The grams of activator used for a stock solution of 250 g are obtained from the equation $35x=3(250+x)$, and thus $x=23.44$. Accordingly, the composition of the activator is 35% w/w of hydrogen peroxide, provided as 23.44 g per 250 g of parent solution, which is equal to 9.38 g/100 g of parent solution.

The properties of the activator match those of commercial hydrogen peroxide, that is to say:

| Property | Unit of measure | Values |
|---|---|---|
| Specific gravity at 20° C. | g/ml | 1.132 |
| pH (10% w/w in deionized water) at 20° C. | U of pH | 2.00–3.00 |
| Vapor pressure at 20° C. | mbar | 17–20 |
| Miscibility in water | | full |
| Appearance | | clear |
| Color | | colorless |
| Odor | | slightly pungent |

EXAMPLE 2

The same procedure as that in Example 1 was followed and a parent solution was prepared having the following percentage composition:

| Component | % w/w | g per 250 g of solution |
|---|---|---|
| Deionized water | 46 | 115 |
| Concentrated sulfuric acid (96%) | 1 | 2.5 |

-continued

| Component | % w/w | g per 250 g of solution |
|---|---|---|
| Isopropyl alcohol | 25 | 62.5 |
| Glacial acetic acid | 28 | 70 |

Isopropyl alcohol at concentrations of about 20% or higher (see (1*) Leaper S. 1984b, Synergistic killing of spores of *bacillus subtilis* by peracetic acid and alcohol—J. Food Technol., 19–355) has a synergistic effect with PAA as regards its germicidal activity. At the same time, the addition of this component allows the amount of water to be reduced, thus reversing the peracetic acid formation equilibrium.

Moreover, from the organoleptic point of view the addition of alcohol decreases the pungent odor of the acetic acid.

The components were mixed in the above mentioned sequence. After addition of the components, stirring was performed for 15 minutes, then the system was left to rest for 10 minutes; a sample was then taken in order to determine the physical-chemical characteristics, which were found to be as follows.

| Property | Unit of measure | Values |
|---|---|---|
| Specific gravity at 20° C. | g/ml | 0.983 ± 0.010 |
| pH (10% w/w in deionized water) at 20° C. | U of pH | 1.00–2.00 |
| Miscibility in water | | full |
| Appearance | | clear |
| Color | | colorless |

A solution of hydrogen peroxide (35% w/w) was used as activator. The grams of activator used for a 250 g parent solution were determined as follows: $35 \cdot x = 3 \cdot (250+x)$, and thus $x=23.44$. Accordingly, the composition of the activator was:

| | g per 100 g of parent solution | g per 250 g of parent solution |
|---|---|---|
| Hydrogen peroxide, 35% w/w | 9.38 | 23.44 |

The chemical-physical properties of the activator were those listed in Example 1.

After activation, the chemical-physical properties of the activated solution were as follows:

| Property | Unit of measure | Values |
|---|---|---|
| Specific gravity at 20° C. | g/ml | 0.992 ± 0.010 |
| pH (10% w/w in deionized water) at 20° C. | U of pH | 1.71 ± 0.10 |
| Miscibility in water | | full |
| Appearance | | clear |
| Color | | colorless |

EXAMPLE 3

The same procedure as that in Example 2 was followed for preparing a parent solution having the following percentage composition:

| Component | % w/w | g per 250 g of solution |
|---|---|---|
| Deionized water | 46 | 115 |
| Concentrated sulfuric acid (96%) | 1 | 2.5 |
| Ethyl alcohol | 25 | 62.5 |
| Glacial acetic acid | 28 | 70 |

Ethyl alcohol at concentrations of about 20% (see (1*) above) has a synergistic effect with PAA as regards its germicidal activity. At the same time, the addition of this component allows the amount of water to be reduced, thus reversing peracetic acid formation equilibrium.

The components were mixed in the above-mentioned sequence. After addition of the components, stirring was performed for 15 minutes, the system was then left to rest for 10 minutes, after which a sample was taken to determine the physical and chemical characteristics, which were found to be as follows:

| Property | Unit of measure | Values |
|---|---|---|
| Specific gravity at 20° C. | g/ml | 0.984 ± 0.010 |
| pH (10% w/w in deionized water) at 20° C. | U of pH | 1.00–2.00 |
| Miscibility in water | | Full |
| Color | | Colorless |

A 35% w/w solution of HP was used as an activator. The grams of activator used for a 250 g parent solution were determined as follows: $35 \cdot x = 3 \cdot (250+x)$, and thus $x=23.44$. Accordingly, the composition of the activator was:

| | g per 100 g of parent solution | g per 250 g of parent solution |
|---|---|---|
| Hydrogen peroxide, 35% w/w | 9.38 | 23.44 |

The chemical-physical properties of the activator were those listed in Example 1.

After activation, the activated solution had the following chemical-physical properties:

| Property | Unit of measure | Values |
|---|---|---|
| Specific gravity at 20° C. | g/ml | 0.994 ± 0.010 |
| pH (10% w/w in deionized water) at 20° C. | U of pH | 1.70 ± 0.10 |
| Miscibility in water | | full |
| Appearance | | clear |
| Color | | colorless |

EXAMPLE 4

The same procedure as that in Example 3 was followed for preparing a parent solution having the following percentage composition:

| Component | % w/w | g per 250 g of solution |
|---|---|---|
| Deionized water | 44.5 | 111.25 |
| Concentrated sulfuric acid (96%) | 1 | 2.5 |
| Ethyl alcohol | 25 | 62.5 |
| Anionic surfactant | 1.5 | 3.75 |
| Glacial acetic acid | 28 | 70 |

A sodium alkylbenzene sulfonate with a medium alkyl chain and with a strong acid character, and thus fully dissociated in acid conditions, was used as an anionic surfactant. Alkylsulfone or alkyl ether sulfone derivatives compatible with the acid environment are thus preferred as anionic surfactant components.

The presence of an anionic surfactant component not only ensures higher stability but also a higher antimicrobial activity of the diluted solutions of PAA.

The components were mixed according to the above listed sequence. After addition of the components, the system was stirred for 15 minutes and then left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 0.985 ± 0.010 |
| pH (10% w/w in deionized water) at 20° C. | U of pH | 1.00–2.00 |
| Miscibility in water | | full |
| Appearance | | clear |
| Color | | colorless |

A 35% w/w solution of HP was used as an activator. The grams of activator used for a 250 g parent solution were determined as follows: 35.x=3.(250+x), and thus x=23.44. Accordingly, the composition of the activator was:

| | g per 100 g of parent solution | g per 250 g of parent solution |
|---|---|---|
| Hydrogen peroxide, 35% w/w | 9.38 | 23.44 |

The chemical-physical properties of the activator were those listed in Example 1.

After activation, the activated solution had the following chemical-physical properties:

| Property | Unit of measure | Values |
|---|---|---|
| Specific gravity at 20° C. | g/ml | 0.993 ± 0.010 |
| pH (10% w/w in deionized water) at 20° C. | U of pH | 1.70 ± 0.10 |
| Miscibility in water | | full |
| Appearance | | clear |
| Color | | colorless |

EXAMPLE 5

The same procedure as that in Example 4 was followed for preparing a parent solution having the following percentage composition:

| Component | % w/w | g per 250 g of solution |
|---|---|---|
| Deionized water | 44 | 110 |
| Concentrated sulfuric acid (96%) | 1 | 2.5 |
| Ethyl alcohol | 25 | 62.5 |
| Anionic surfactant | 1.5 | 3.75 |
| Stabilizing agent | 0.5 | 1.25 |
| Glacial acetic acid | 28 | 70 |

The stabilizing agent is constituted by a sequestrant, such as sodium pyrophosphate, or by a chelating agent, such as 8-hydroxyquinoline, which is designed to remove the traces of metallic ions that accelerate the decomposition of peroxides.

The components were mixed according to the above listed sequence. After addition of the components, the system was stirred for 15 minutes and then left to rest for 10 minutes, after which a sample was taken to determine the physical-chemical characteristics, which were found to be as follows:

| Property | Unit of measure | Values |
|---|---|---|
| Specific gravity at 20° C. | g/ml | 0.986 ± 0.010 |
| pH (10% w/w in deionized water) at 20° C. | U of pH | 1.00–2.00 |
| Miscibility in water | | full |
| Appearance | | clear |
| Color | | colorless |

A 35% w/w solution of HP was used as an activator. The grams of activator used for a 250 g parent solution were determined as follows: 35.x=3.(250+x), from which x=23.44. Accordingly, the composition of the activator was:

| | g per 100 g of stock solution | g per 250 g of stock solution |
|---|---|---|
| Hydrogen peroxide, 35% w/w | 9.38 | 23.44 |

The chemical-physical properties of the activator were those listed in Example 1.

After activation, the activated solution had the following chemical-physical properties:

| Property | Unit of measure | Values |
|---|---|---|
| Specific gravity at 20° C. | g/ml | 0.993 ± 0.010 |
| pH (10% by weight in deionized water) at 20° C. | U of pH | 1.70 ± 0.10 |
| Miscibility in water | | full |
| Appearance | | clear |
| Color | | colorless |

EXAMPLE 6

The same procedure as that in the Example 5 was followed for preparing a parent solution which had the following percentage composition:

| Component | % w/w | g per 250 g of solution |
|---|---|---|
| Deionized water | 44 | 110 |
| Concentrated sulfuric acid (96%) | 1 | 2.5 |
| Ethyl alcohol | 25 | 62.5 |
| Anionic surfactant | 1.5 | 3.75 |
| Stabilizing agent | 0.5 | 1.25 |
| Glacial acetic acid | 28 | 70 |

The components were mixed according to the above listed sequence. After addition of the components, the system was stirred for 15 minutes and then left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 0.986 ± 0.010 |
| pH (10% w/w in deionized water) at 20° C. | U of pH | 1.00–2.00 |
| Miscibility in water | | full |
| Appearance | | clear |
| Color | | colorless |

A 50% w/w solution of HP was used as an activator. The grams of activator used for a 250 g parent solution were determined as follows: 50.x=3.(250+x), from which x=15.96. Accordingly, the composition of the activator was:

| | g per 100 g of parent solution | g per 250 g of parent solution |
|---|---|---|
| Hydrogen peroxide, 50% w/w | 6.38 | 15.96 |

The chemical-physical properties of the activator were as follows:

| Property | Unit of measure | Values |
|---|---|---|
| Specific gravity at 20° C. | g/ml | 1.280 |
| pH (10% w/w in deionized water) at 20° C. | U of pH | 2.00–3.00 |
| Miscibility in water | | full |
| Appearance | | clear |
| Color | | colorless |
| Odor | | slightly pungent |

After activation, the activated solution had the following chemical-physical properties:

| Property | Unit of measure | Values |
|---|---|---|
| Specific gravity at 20° C. | g/ml | 0.995 ± 0.010 |
| pH (10% w/w in deionized water) at 20° C. | U of pH | 1.70 ± 0.10 |
| Miscibility in water | | full |
| Appearance | | clear |
| Color | | colorless |

EXAMPLE 7

The same procedure as that in Example 1 was followed for preparing a parent solution which had the following percentage composition:

| Component | % w/w | g per 250 g of solution |
|---|---|---|
| Deionized water | 43 | 107.5 |
| Concentrated sulfuric acid (96%) | 1 | 2.5 |
| Glacial acetic acid | 56 | 70 |

The components were mixed according to the above listed sequence. After addition of the components, the system was stirred for 15 minutes and then left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 1.055 ± 0.010 |
| pH (10% w/w in deionized water) at 20° C. | U of pH | 1.00–2.00 |
| Miscibility in water | | full |
| Appearance | | clear |
| Color | | colorless |

A 35% w/w solution of HP was used as an activator. The grams of activator used for a 250 g parent solution were determined as follows: 35.x=3.(250+x), from which x=23.44. Accordingly, the composition of the activator was:

|  | g per 100 g of parent solution | g per 250 g of parent solution |
|---|---|---|
| Hydrogen peroxide, 35% w/w | 9.38 | 23.44 |

The chemical-physical properties of the activator were those listed in Example 1:

After activation, the activated solution had the following chemical-physical properties:

| Property | Unit of measure | Values |
|---|---|---|
| Specific gravity at 20° C. | g/ml | 1.064 ± 0.010 |
| pH (10% w/w in deionized water) at 20° C. | U of pH | 1.75 ± 0.10 |
| Miscibility in water |  | full |
| Appearance |  | clear |
| Color |  | colorless |

EXAMPLE 8

The same procedure as Example 2 was followed, preparing a stock solution which had the following percentage composition:

| Component | % w/w | g per 250 g of solution |
|---|---|---|
| Deionized water | 28 | 70 |
| Concentrated sulfuric acid (96%) | 1 | 2.5 |
| Isopropyl alcohol | 15 | 37.5 |
| Glacial acetic acid | 56 | 140 |

The components were mixed according to the above listed sequence. After addition of the components, the system was stirred for 15 minutes and then left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 0.990 ± 0.010 |
| pH (10% w/w in deionized water) at 20° C. | U of pH | 1.00–2.00 |
| Miscibility in water |  | full |
| Appearance |  | clear |
| Color |  | colorless |

A 35% w/w solution of HP was used as an activator. The grams of activator used for a 250 g parent solution were determined as follows: 35.x=3.(250+x), from which x=23.44. Accordingly, the composition of the activator was:

|  | g per 100 g of parent solution | g per 250 g of parent solution |
|---|---|---|
| Hydrogen peroxide, 35% w/w | 9.38 | 23.44 |

The chemical-physical properties of the activator were those listed in Example 1:

After activation, the activated solution had the following chemical-physical properties:

| Property | Unit of measure | Values |
|---|---|---|
| Relative density at 20° C. | g/ml | 0.998 ± 0.010 |
| pH (10% w/w in deionized water) at 20° C. | U of pH | 1.70 ± 0.10 |
| Miscibility in water |  | full |
| Appearance |  | clear |
| Color |  | colorless |

EXAMPLE 9

The same procedure as Example 8 was followed, preparing a stock solution which had the following percentage composition:

| Component | % w/w | g per 250 g of solution |
|---|---|---|
| Deionized water | 18 | 45 |
| Concentrated sulfuric acid (96%) | 1 | 2.5 |
| Isopropyl alcohol | 25 | 62.5 |
| Glacial acetic acid | 56 | 140 |

The components were mixed according to the above listed sequence. After introducing the components, the system was subjected to agitation for 15 minutes and then was left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 0.986 ± 0.010 |
| pH (10% w/w in deionized water) at 20° C. | U of pH | 1.00–2.00 |
| Miscibility in water |  | full |
| Appearance |  | clear |
| Color |  | colorless |

A 35% w/w solution of HP was used as an activator. The grams of activator used for a 250 g parent solution were determined as follows: 35.x=3.(250+x), from which x=23.44. Accordingly, the composition of the activator was:

|  | g per 100 g of parent solution | g per 250 g of parent solution |
|---|---|---|
| Hydrogen peroxide, 35% w/w | 9.38 | 23.44 |

The chemical-physical properties of the activator were those listed in Example 1:

After activation, the activated solution had the following chemical-physical properties:

| Property | Unit of measure | Values |
|---|---|---|
| Specific gravity at 20° C. | g/ml | 0.995 ± 0.010 |
| pH (10% w/w in deionized water) at 20° C. | U of pH | 1.69 ± 0.10 |
| Miscibility in water |  | full |
| Appearance |  | clear |
| Color |  | colorless |

EXAMPLE 10

The same procedure as that in Example 9 was followed for preparing a stock solution which had the following percentage composition:

| Component | % w/w | g per 250 g of solution |
|---|---|---|
| Deionized water | 16.5 | 41.25 |
| Concentrated sulfuric acid (96%) | 1 | 2.5 |
| Isopropyl alcohol | 25 | 62.5 |
| Anionic surfactant | 1.5 | 3.75 |
| Glacial acetic acid | 56 | 140 |

The components were mixed according to the above listed sequence. After addition of the components, the system was stirred for 15 minutes and then left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 0.987 ± 0.010 |
| pH (10% w/w in deionized water) at 20° C. | U of pH | 1.00–2.00 |
| Miscibility in water |  | full |
| Appearance |  | clear |
| Color |  | colorless |

A 35% w/w solution of HP was used as an activator. The grams of activator used for a 250 g parent solution were determined as follows: 35.x=3.(250+x), from which x=23.44. Accordingly, the composition of the activator was:

|  | g per 100 g of parent solution | g per 250 g of parent solution |
|---|---|---|
| Hydrogen peroxide, 35% w/w | 9.38 | 23.44 |

The chemical-physical properties of the activator were those listed in Example 1:

After activation, the activated solution had the following chemical-physical properties:

| Property | Unit of measure | Values |
|---|---|---|
| Specific gravity at 20° C. | g/ml | 0.995 ± 0.010 |
| pH (10% w/w in deionized water) at 20° C. | U of pH | 1.70 ± 0.10 |
| Miscibility in water |  | full |
| Appearance |  | clear |
| Color |  | colorless |

EXAMPLE 11

The same procedure as that in Example 5 was followed for preparing a parent solution which had the following percentage composition:

| Component | % w/w | g per 250 g of solution |
|---|---|---|
| Deionized water | 16 | 40 |
| Concentrated sulfuric acid (96%) | 1 | 2.5 |
| Isopropyl alcohol | 25 | 62.5 |
| Anionic surfactant | 1.5 | 3.75 |
| Stabilizing agent | 0.5 | 1.25 |
| Glacial acetic acid | 56 | 140 |

The components were mixed according to the above listed sequence. After addition of the components, the system was stirred for 15 minutes and then left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 0.986 ± 0.010 |
| pH (10% w/w in deionized water) at 20° C. | U of pH | 1.00–2.00 |
| Miscibility in water |  | full |
| Appearance |  | clear |
| Color |  | colorless |

A 35% w/w solution of HP was used as an activator. The grams of activator used for a 250 g parent solution were determined as follows: $35 \cdot x = 3 \cdot (250+x)$, from which $x=23.44$. Accordingly, the composition of the activator was:

|  | g per 100 g of parent solution | g per 250 g of parent solution |
|---|---|---|
| Hydrogen peroxide, 35% w/w | 9.38 | 23.44 |

The chemical-physical properties of the activator were those listed in Example 1:

After activation, the activated solution had the following chemical-physical properties:

| Property | Unit of measure | Values |
|---|---|---|
| Specific gravity at 20° C. | g/ml | 0.996 ± 0.010 |
| pH (10% w/w in deionized water) at 20° C. | U of pH | 1.71 ± 0.10 |
| Miscibility in water |  | full |
| Appearance |  | clear |
| Color |  | colorless |

EXAMPLE 12

The same procedure as that in Example 11 was followed, preparing a stock solution which had the following percentage composition:

| Component | % w/w | g per 250 g of solution |
|---|---|---|
| Deionized water | 16 | 40 |
| Concentrated sulfuric acid (96%) | 1 | 2.5 |
| Isopropyl alcohol | 25 | 62.5 |
| Anionic surfactant | 1.5 | 3.75 |
| Stabilizing agent | 0.5 | 1.25 |
| Glacial acetic acid | 56 | 140 |

The components were mixed according to the above listed sequence. After addition of the components, the system was stirred for 15 minutes and then left to rest for 10 minutes, after which a sample was taken in order to determine the physical-chemical characteristics, which were found to be as in Example 11:

A 50% w/w solution of HP was used as an activator. The grams of activator used for a 250 g parent solution were determined as follows: $50 \cdot x = 3 \cdot (250+x)$, from which $x=15.96$. Accordingly, the composition of the activator was:

|  | g per 100 g of parent solution | g per 250 g of parent solution |
|---|---|---|
| Hydrogen peroxide, 50% w/w | 6.38 | 15.96 |

The chemical-physical properties of the activator were those listed in Example 6:

After activation, the activated solution had the following chemical-physical properties:

| Property | Unit of measure | Values |
|---|---|---|
| Relative density at 20° C. | g/ml | 0.996 ± 0.010 |
| pH (10% w/w in deionized water) at 20° C. | U of pH | 1.71 ± 0.10 |
| Miscibility in water |  | full |
| Appearance |  | clear |
| Color |  | colorless |

EXAMPLE 13

The same procedure as that in Example 7 was followed for preparing a parent solution which had the following percentage composition:

| Component | % w/w | g per 250 g of solution |
|---|---|---|
| Deionized water | 57 | 142.5 |
| Concentrated sulfuric acid (96%) | 1 | 2.5 |
| Glacial acetic acid | 42 | 105 |

The components were mixed according to the above listed sequence. After addition of the components, the system was stirred for 15 minutes and then left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 1.040 ± 0.010 |
| pH (10% w/w in deionized water) at 20° C. | U of pH | 1.00–2.00 |
| Miscibility in water |  | full |
| Appearance |  | clear |
| Color |  | colorless |

A 35% w/w solution of HP was used as an activator. The grams of activator used for a 250 g parent solution were determined as follows: $35 \cdot x = 3 \cdot (250+x)$, from which $x=23.44$. Accordingly, the composition of the activator was:

|  | g per 100 g of parent solution | g per 250 g of parent solution |
|---|---|---|
| Hydrogen peroxide, 35% w/w | 9.38 | 23.44 |

The chemical-physical properties of the activator were those listed in Example 1:

After activation, the activated solution had the following chemical-physical properties:

| Property | Unit of measure | Values |
|---|---|---|
| Specific gravity at 20° C. | g/ml | 1.052 ± 0.010 |
| pH (10% w/w in deionized water) at 20° C. | U of pH | 1.66 ± 0.10 |

-continued

| Property | Unit of measure | Values |
|---|---|---|
| Miscibility in water | | full |
| Appearance | | clear |
| Color | | colorless |

EXAMPLE 14

The same procedure as that in Example 13 was followed for preparing a parent solution which had the following percentage composition:

| Component | % w/w | g per 250 g of solution |
|---|---|---|
| Deionized water | 79 | 197.5 |
| Concentrated sulfuric acid (96%) | 1 | 2.5 |
| Glacial acetic acid | 20 | 50 |

The components were mixed according to the above listed sequence. After addition of the components, the system was stirred for 15 minutes and then left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 1.023 ± 0.010 |
| pH (10% w/w in deionized water) at 20° C. | U of pH | 1.00–2.00 |
| Miscibility in water | | full |
| Appearance | | clear |
| Color | | colorless |

A 35% w/w solution of HP was used as an activator. The grams of activator used for a 250 g parent solution were determined as follows: $35 \cdot x = 3 \cdot (250+x)$, from which $x=23.44$. Accordingly, the composition of the activator was:

| | g per 100 g of parent solution | g per 250 g of parent solution |
|---|---|---|
| Hydrogen peroxide, 35% w/w | 9.38 | 23.44 |

The chemical-physical properties of the activator were those listed in Example 1:

After activation, the activated solution had the following chemical-physical properties:

| Property | Unit of measure | Values |
|---|---|---|
| Specific gravity at 20° C. | g/ml | 1.033 ± 0.010 |
| pH (10% w/w in deionized water) at 20° C. | U of pH | 1.59 ± 0.10 |
| Miscibility in water | | full |
| Appearance | | clear |
| Color | | colorless |

EXAMPLE 15

The same procedure as that in Example 14 was followed for preparing a parent solution which had the following percentage composition:

| Component | % w/w | g per 250 g of solution |
|---|---|---|
| Deionized water | 29 | 72.5 |
| Concentrated sulfuric acid (96%) | 1 | 2.5 |
| Glacial acetic acid | 70 | 175 |

The components were mixed according to the above listed sequence. After addition of the components, the system was stirred for 15 minutes and then left to rest for 10 minutes, after which a sample was taken in order to determine the physical-chemical characteristics, which were found to be as follows:

| Property | Unit of measure | Values |
|---|---|---|
| Specific gravity at 20° C. | g/ml | 1.066 ± 0.010 |
| pH (10% w/w in deionized water) at 20° C. | U of pH | 1.00–2.00 |
| Miscibility in water | | full |
| Appearance | | clear |
| Color | | colorless |

A 35% w/w solution of HP was used as an activator. The grams of activator used for a 250 g parent solution were determined as follows: $35 \cdot x = 3 \cdot (250+x)$, from which $x=23.44$. Accordingly, the composition of the activator was:

| | g per 100 g of parent solution | g per 250 g of parent solution |
|---|---|---|
| Hydrogen peroxide, 35% w/w | 9.38 | 23.44 |

The chemical-physical properties of the activator were those listed in Example 1:

After activation, the activated solution had the following chemical-physical properties:

| Property | Unit of measure | Values |
|---|---|---|
| Specific gravity at 20° C. | G/ml | 1.076 ± 0.010 |
| pH (10% w/w in deionized water) at 20° C. | U of pH | 1.46 ± 0.10 |
| Miscibility in water | | full |
| Appearance | | clear |
| Color | | colorless |

The disinfectant solutions based on peracetic acid prepared just before use with the method according to the present invention are now compared with currently commercially available solutions, that is to say:

EXAMPLE 16

A parent solution according to the present invention having the following composition was prepared:

| Component | % w/w | g per 250 g of solution |
| --- | --- | --- |
| Deionized water | 98.800 | 247.000 |
| Tetraacetyl glycoluryle (TAGU) | 1.200 | 3.000 |

The instruments of Example 1 were used for this preparation.

The above components were weighed separately. In order to solubilize the tetraacetyl glycoluryle, the water was heated to approximately 70–80° C. while stirring. After addition of the components, further stirring was performed for 15 minutes and the product was left to rest for 10 minutes.

The activator used was carbamide peroxide with 35% w/w $H_2O_2$ in the amount of 5 g per 250 g of parent solution, which means 2 g per 100 g of parent solution. The properties of this activator match those of the active principle.

EXAMPLE 17

A parent solution having the following composition was prepared:

| Component | % w/w | g per 250 g of solution |
| --- | --- | --- |
| Deionized water | 88.800 | 222.000 |
| Tetraacetyl glycoluryl (TAGU) | 1.200 | 3.000 |
| Glacial acetic acid | 10.000 | 25.000 |

The instruments of Example 1 were used for this preparation.

The above components were weighed separately. In order to solubilize the tetraacetyl glycoluryle, the water was heated to approximately 70–80° C. while stirring. After cooling the solution to 20° C., glacial acetic acid was added. After addition of the components, further stirring was performed for 15 minutes and the product was left to rest for 10 minutes.

The activator used was 35% w/w hydrogen peroxide, in the amount of 5 g per 250 g of parent solution, which means 2 g per 100 g of parent solution. The properties of this activator match those of the active principle.

EXAMPLE 18

A parent solution having the following composition was prepared:

| Component | % w/w | g per 250 g of solution |
| --- | --- | --- |
| Deionized water | 78.800 | 197.000 |
| Tetraacetyl glycoluryle (TAGU) | 1.200 | 3.000 |
| Glacial acetic acid | 10.000 | 25.000 |
| Isopropyl alcohol | 10.000 | 25.000 |

The instruments of Example 1 were used for this preparation.

The above components were weighed separately. In order to solubilize the tetraacetyl glycoluryle, the water was heated to approximately 70–80° C. under agitation. After cooling the solution to 20° C., glacial acetic acid and the isopropyl alcohol were added. After addition of the components, further stirring was performed for 15 minutes and the product was left to rest for 10 minutes.

At these concentrations, isopropyl alcohol has a synergistic effect with peracetic acid as regards its germicidal activity. At the same time, the addition of this component allows the amount of water to be decreased while reversing the peracetic acid formation equilibrium.

Furthermore, from the organoleptic point of view the addition of alcohol reduces the pungent odor of acetic acid and acts as a preservative for the parent solution before activation.

The activator used was 35% w/w hydrogen peroxide, in the amount of 5 g per 250 g of parent solution, which means 2 g per 100 g of parent solution. The properties of this activator match those of the active principle.

EXAMPLE 19

A parent solution having the following composition was prepared:

| Component | % w/w | g per 250 g of solution |
| --- | --- | --- |
| Deionized water | 77.300 | 193.250 |
| Tetraacetyl glycoluryle (TAGU) | 1.200 | 3.000 |
| Glacial acetic acid | 10.000 | 25.000 |
| Isopropyl alcohol | 10.000 | 25.000 |
| Stabilizing agent (dimethyl amino methane diphosphonic acid) | 1.500 | 3.750 |

The instruments of Example 1 were used for this preparation.

The above components were weighed separately. In order to solubilize the tetraacetyl glycoluryle, the water was heated to approximately 70–80° C. while stirring. After cooling the solution to 20° C., glacial acetic acid, isopropyl alcohol and stabilizing agent were added. After addition of the components, further stirring was performed for 15 minutes and the product was left to rest for 10 minutes.

The activator used was carbamide peroxide with 35% w/w $H_2O_2$ in the amount of 5 g per 250 g of parent solution, which means 2 g per 100 g of parent solution. The properties of this activator match those of the active principle.

EXAMPLE 20

A parent solution having the following composition was prepared:

| Component | % w/w | g per 250 g of solution |
| --- | --- | --- |
| Deionized water | 75.800 | 189.500 |
| Tetraacetyl glycoluryle (TAGU) | 1.200 | 3.000 |
| Glacial acetic acid | 10.000 | 25.000 |
| Isopropyl alcohol | 10.000 | 25.000 |

-continued

| Component | % w/w | g per 250 g of solution |
|---|---|---|
| Stabilizing agent (dimethyl amino methane diphosphonic acid) | 1.500 | 3.750 |
| Sodium alkyl (C-12) benzene sulfonate | 1.500 | 3.750 |

The instruments of Example 1 were used for this preparation.

The above components were weighed separately. In order to solubilize the tetraacetyl glycoluryle, the water was heated to approximately 70–80° C. while stirring. After cooling the solution to 20° C., glacial acetic acid, isopropyl alcohol, stabilizing agent and anionic surfactant were added. After addition of the components, further stirring was performed for 15 minutes and the product was left to rest for 10 minutes.

The activator used was 35% w/w hydrogen peroxide, in the amount of 5 g per 250 g of parent solution, which means 2 g per 100 g of parent solution. The properties of this activator match those of the active principle.

EXAMPLE 21

A parent solution having the following composition was prepared:

| Component | % w/w | g per 250 g of solution |
|---|---|---|
| Deionized water | 73.800 | 184.500 |
| Tetraacetyl glycoluryle (TAGU) | 1.200 | 3.000 |
| Glacial acetic acid | 10.000 | 25.000 |
| Isopropyl alcohol | 10.000 | 25.000 |
| Stabilizing agent (dimethyl amino methane diphosphonic acid) | 1.500 | 3.750 |
| Sodium alkyl (C-12) benzene sulfonate | 1.500 | 3.750 |
| Propylene glycol (wetting agent) | 2.000 | 5.000 |

The instruments of Example 1 were used for this preparation.

The above components were weighed separately. In order to solubilize the tetraacetyl glycoluryle, the water was heated to approximately 70–80° C. while stirring. After cooling the solution to 20° C., glacial acetic acid, isopropyl alcohol, stabilizing agent, surfactant and wetting agent were added. After addition of the components, further stirring was performed for 15 minutes and the product was left to rest for 10 minutes.

The activator used was 35% w/w hydrogen peroxide in the amount of 5 g per 250 g of parent solution, which means 2 g per 100 g of parent solution. The properties of this activator match those of the active principle.

EXAMPLE 22

A parent solution having the following composition was prepared:

| Component | % w/w | g per 250 g of solution |
|---|---|---|
| Deionized water | 53.800 | 134.500 |
| Tetraacetyl glycoluryle (TAGU) | 1.200 | 3.000 |
| Glacial acetic acid | 10.000 | 25.000 |
| Isopropyl alcohol | 10.000 | 25.000 |
| Stabilizing agent (dimethyl amino methane diphosphonic acid) | 1.500 | 3.750 |
| Sodium alkyl (C-12) benzene sulfonate | 1.500 | 3.750 |
| Propylene glycol (wetting agent) | 2.000 | 5.000 |
| Sodium acetate | 20.000 | 50.000 |

The instruments of Example 1 were used for this preparation.

The above components were weighed separately. In order to solubilize the tetraacetyl glycoluryle, the water was heated to approximately 70–80° C. while stirring. After cooling the solution to 20° C., the glacial acetic acid, the isopropyl alcohol, the stabilizing agent, the anionic surfactant, the wetting agent and the sodium acetate were added, so as to buffer the pH of the parent solution in the range from 3.50 to 7.00 at 20° C. After addition of the components, further stirring was performed for 15 minutes and the product was left to rest for 10 minutes.

The activator used was 35% w/w hydrogen peroxide in the amount of 5 g per 250 g of parent solution, which means 2 g per 100 g of parent solution. The properties of this activator match those of the active principle.

EXAMPLE 23

A parent solution having the following composition was prepared:

| Component | % w/w | g per 250 g of solution |
|---|---|---|
| Deionized water | 81.300 | 203.250 |
| Tetraacetyl glycoluryle (TAGU) | 1.200 | 3.000 |
| Glacial acetic acid | 1.000 | 2.500 |
| Isopropyl alcohol | 10.000 | 25.000 |
| Stabilizing agent (dimethyl amino methane diphosphonic acid) | 1.500 | 3.750 |
| Sodium alkyl (C-12) benzene sulfonate | 1.500 | 3.750 |
| Propylene glycol (wetting agent) | 2.000 | 5.000 |
| Sodium hydroxide | 1.500 | 3.750 |

The instruments of Example 1 were used for this preparation.

The above components were weighed separately. In order to solubilize the tetraacetyl glycoluryle, the water was heated to approximately 70–80° C. while stirring. After cooling the solution to 20° C., the glacial acetic acid, the isopropyl alcohol, the stabilizing agent, the anionic surfactant and the wetting agent were added, followed by the sodium hydroxide in order to buffer the pH of the parent solution within the range 3.50 to 7.00 at 20° C. After addition of the components, further stirring was performed for 15 minutes and the product was left to rest for 10 minutes.

The activator used was 35% w/w hydrogen peroxide in the amount of 5 g per 250 g of parent solution, which means 2 g per 100 g of parent solution. The properties of this activator match those of the active principle.

EXAMPLE 24

A parent solution having the following composition was prepared:

| Component | % w/w | g per 250 g of solution |
|---|---|---|
| Deionized water | 81.300 | 203.250 |
| Tetraacetyl glycoluryle (TAGU) | 1.200 | 3.000 |
| Glacial acetic acid | 1.000 | 2.500 |
| Isopropyl alcohol | 10.000 | 25.000 |
| Stabilizing agent (dimethyl amino methane diphosphonic acid) | 1.500 | 3.750 |
| Sodium alkyl (C-12) benzene sulfonate | 1.500 | 3.750 |
| Propylene glycol (wetting agent) | 2.000 | 5.000 |
| Sodium carbonate | 1.500 | 3.750 |

The instruments of Example 1 were used for this preparation.

The above components were weighed separately. In order to solubilize the tetraacetyl glycoluryle, the water was heated to approximately 70–80° C. while stirring. After cooling the solution to 20° C., the glacial acetic acid, the isopropyl alcohol, the stabilizing agent, the anionic surfactant and the wetting agent were added, followed by the sodium carbonate in order to buffer the pH of the stock solution within the range 3.50 to 7.00 at 20° C. After addition of the components, further stirring was performed for 15 minutes and the product was left to rest for 10 minutes.

The activator used was 35% w/w hydrogen peroxide in the amount of 5 g per 250 g of parent solution, which means 2 g per 100 g of parent solution. The properties of this activator match those of the active principle.

EXAMPLE 25

A parent solution having the following composition was prepared:

| Component | % w/w | g per 250 g of solution |
|---|---|---|
| Deionized water | 81.300 | 203.250 |
| Tetraacetyl glycoluryle (TAGU) | 1.200 | 3.000 |
| Glacial acetic acid | 1.000 | 2.500 |
| Isopropyl alcohol | 10.000 | 25.000 |
| Stabilizing agent (dimethyl amino methane diphosphonic acid) | 1.500 | 3.750 |
| Sodium alkyl (C-12) benzene sulfonate | 1.500 | 3.750 |
| Propylene glycol (wetting agent) | 2.000 | 5.000 |
| Sodium carbonate | 1.500 | 3.750 |

The instruments of Example 1 were used for this preparation.

The above components were weighed separately. In order to solubilize the tetraacetyl glycoluryle, the water was heated to approximately 70–80° C. while stirring. After cooling the solution to 20° C., the glacial acetic acid, the isopropyl alcohol, the stabilizing agent, the anionic surfactant and the wetting agent were added, followed by the sodium carbonate in order to buffer the pH of the stock solution within the range from 3.50 to 7.00 at 20° C. After addition of the components, further stirring was performed for 15 minutes and the product was left to rest for 10 minutes.

The activator used was carbamide peroxide with 35% w/w $H_2O_2$ in the amount of 5 g per 250 g of parent solution, which means 2 g per 100 g of parent solution. The properties of this activator match those of the active principle.

EXAMPLE 26

A parent solution having the following composition was prepared:

| Component | % w/w | g per 250 g of solution |
|---|---|---|
| Deionized water | 81.299 | 203.248 |
| Tetraacetyl glycoluryle (TAGU) | 1.200 | 3.000 |
| Glacial acetic acid | 1.000 | 2.500 |
| Isopropyl alcohol | 10.000 | 25.000 |
| Stabilizing agent (dimethyl amino methane diphosphonic acid) | 1.500 | 3.750 |
| Sodium alkyl (C-12) benzene sulfonate | 1.500 | 3.750 |
| Propylene glycol (wetting agent) | 2.000 | 5.000 |
| Sodium carbonate | 1.500 | 3.750 |
| Amaranth red | 0.00065 | 0.002 |

The instruments of Example 1 were used for this preparation.

The above components were weighed separately. In order to solubilize the tetraacetyl glycoluryle, the water was heated to approximately 70–80 C. under agitation. After cooling the solution to 20° C., the glacial acetic acid, the isopropyl alcohol, the stabilizing agent, the anionic surfactant and the wetting agent were added, followed by the sodium carbonate in order to buffer the pH of the stock solution within the 3.50–7.00 range at 20° C., finally adding the oxide-reduction indicator.

After addition of the components, further stirring was performed for 15 minutes and the product was left to rest for 10 minutes. The indicator, added at the end, gives the parent solution a color which changes when activator is added, thus assisting the operator in identifying activated solutions.

As indicator any compound or double conjugate bond complex can be used which changes color depending upon its state of oxidation.

The activator used was carbamide peroxide with 35% w/w $H_2O_2$ in the amount of 5 g per 250 g of parent solution, which means 2 g per 100 g of parent solution. The properties of this activator match those of the active principle.

EXAMPLE 27

A parent solution having the following composition was prepared:

| Component | % w/w | g per 250 g of solution |
|---|---|---|
| Deionized water | 88.300 | 220.750 |
| Tetraacetyl glycoluryle (TAGU) | 1.200 | 3.000 |
| Glacial acetic acid | 10.000 | 25.000 |
| Concentrated sulfuric acid | 0.500 | 1.250 |

The instruments of Example 1 were used for this preparation.

The above components were weighed separately. In order to solubilize the tetraacetyl glycoluryle, the water was heated to approximately 70–80° C. while stirring. After cooling the solution to 20° C., the glacial acetic acid and the concentrated sulfuric acid were added, taking all precautions with the sulfuric acid for the above mentioned reasons.

After addition of the components, further stirring was performed for 15 minutes and the product was left to rest for 10 minutes.

The activator used was hydrogen peroxide with 35% w/w $H_2O_2$ in the amount of 5 g per 250 g of parent solution, which means 2 g per 100 g of parent solution. The properties of this activator match those of the active principle.

EXAMPLE 28

A parent solution having the following composition was prepared:

| Component | % w/w | g per 250 g of solution |
| --- | --- | --- |
| Deionized water | 89.100 | 222.750 |
| Tetraacetyl ethylene diamine (TAED) | 0.400 | 1.000 |
| Glacial acetic acid | 10.000 | 25.000 |
| Concentrated sulfuric acid | 0.500 | 1.250 |

The instruments of Example 1 were used for this preparation.

The above components were weighed separately. In order to solubilize the tetraacetyl ethylene diamine (TAED), the water was heated to approximately 70–80° C. while stirring. After cooling the solution to 20° C., the glacial acetic acid and the concentrated sulfuric acid were added, taking every precaution with the latter for the above mentioned reasons.

After addition of the components, further stirring was performed for 15 minutes and the product was left to rest for 10 minutes.

The activator used was 35% w/w hydrogen peroxide in the amount of 5 g per 250 g of parent solution, which means 2 g per 100 g of parent solution. The properties of this activator match those of the active principle.

EXAMPLE 29

A parent solution having the following composition was prepared:

| Component | % w/w | g per 250 g of solution |
| --- | --- | --- |
| Deionized water | 83.699 | 209.248 |
| Sodium carbonate | 1.300 | 3.250 |
| Tetraacetyl ethylene diamine (TAED) | 1.000 | 2.500 |
| Glacial acetic acid | 1.000 | 2.500 |
| Isopropyl alcohol | 10.000 | 25.000 |
| Stabilizing agent (dimethyl amino methane diphosphonic acid) | 0.500 | 1.250 |
| Sodium alkyl (C-12) benzene sulfonate | 0.500 | 1.250 |
| Propylene glycol (wetting agent) | 2.000 | 5.000 |
| Amaranth red | 0.001 | 0.002 |

The instruments of Example 1 were used for this preparation.

The above components were weighed separately. In order to solubilize the tetraacetyl ethylene diamine, the water was heated to approximately 70 –80° C. while stirring and after sodium carbonate has been added. After cooling the solution to 20° C., the glacial acetic acid, the isopropyl alcohol, the stabilizing agent, the anionic surfactant, the wetting agent and the oxide-reduction indicator (amaranth red) were added.

After addition of the components, further stirring was performed for 15 minutes and the product was left to rest for 10 minutes.

The activator used was carbamide peroxide with 35% w/w $H_2O_2$ in the amount of 5 g per 250 g of parent solution, which means 2 g per 100 g of parent solution. The properties of this activator match those of the active principle.

EXAMPLE 30

A parent solution having the following composition was prepared:

| Component | % w/w | g per 250 g of solution |
| --- | --- | --- |
| Deionized water | 95.000 | 237.500 |
| Glacial acetic acid | 5.000 | 12.500 |

The instruments of Example 16 were used for this preparation.

The above components were weighed separately. They were then mixed and stirred for 15 minutes and the resulting solution was left to rest for 10 minutes.

The activator used was hydrogen peroxide with 35% w/w $H_2O_2$ in the amount of 5 g per 250 g of parent solution, which means 2 g per 100 g of parent solution. The properties of this activator match those of the active principle.

The disinfectant solutions based on peracetic acid prepared just before use according to the method of the present invention, compared with the currently commercially available solutions, that is to say:

the Peract 20™ solution produced by the Unitrol Division of Minntech Corporation, Minneapolis, USA, composed of:
HP (hydrogen peroxide) 1.00%
PAA (peracetic acid) 0.08%
Inert ingredients 98.92% the Steris 20™ solution produced by the Steris Corporation in Mentor, Ohio, USA, and composed of:
PAA (peracetic acid) 35%, have a much longer stability, as said stability is not linked to the stability of PAA, but to the stability of the peroxide activator, which is less reactive and accordingly more stable.

Moreover, the presence of an alcohol derivative, of an anionic surfactant and of an excess of hydrogen peroxide in the solution ensures, owing to a synergistic effect, an increase in the germicidal activity of the active principle, i.e. peracetic acid.

The solutions based on peracetic acid according to the present invention are highly versatile, since by varying the percentage of the O-acetylated and N-acetylated compounds in the parent solutions, and by varying the percentage of the peroxide activator, it is possible to obtain, more or less rapidly, solutions of peracetic acid in different percentages and with different stability. The reaction for preparation by adding the peroxide activator to the parent solution can be accelerated by means of acid catalysis or better still by adding a strong inorganic acid.

However, this can also be achieved by increasing the percentage in the parent solution of the N-acetylated compound and by reducing the percentage of the O-acetylated compound, since the former is more electrophilic than the latter, i.e. it reacts more rapidly with the peroxide reagent.

The solutions based on peracetic acid according to the present invention are bactericidal, fungicide, tuberclicidal, virucidal and sporicidal for short contact times. The stability of the entire system comprising the activator and the parent solution, stored separately, depends essentially on the stability of the activator. The activator, as mentioned above, loses 1% of its active ingredient per year.

However, this decrease, while being modest in itself, does not affect the efficiency of the entire system, since it has in any case an excess of either the activator or the acetyl substrate with respect to equilibrium which ensures the concentration of peracetic acid required for the intended germicidal effect. The parent solution, in an integral packaging, is stable both from the chemical-physical and the microbiological point of view. The presence of an alcohol compound in fact acts as a preservative for the solution.

Furthermore, the active principles of this solution, i.e. the acetyl substrates, have no detrimental effect in the solution, so much that stability period of the solution can be indicated as 5 years.

The disinfectant power of peracetic acid on medical and surgical instruments in terms of concentration and contact times is widely disclosed and shown in the tables to be found in Seymour S. Block Disinfection, Sterilization and Preservation, 4th edition (1991), pages 172–179.

These tables show that as the concentration of peracetic acid (PAA) increases, contact times decrease. More particularly, the following data were found:

| Microorganisms | Ppm (%) of PAA | Contact times | Effect on medical and surgical instruments |
|---|---|---|---|
| Gram + and Gram – bacteria, fungi and yeasts are inactivated and killed | 100 (0.01%) | 5 minutes or less | Low-level disinfection |
| Gram + and Gram – bacteria, fungi and yeasts are inactivated and killed (in the presence of organic material) | 200–500 | 5 minutes or less | Low-level disinfection |
| Enterovirus | 2000 (0.2%) | 10 to 30 minutes | Primary decontamination |
| Poliovirus (in the presence of yeast extract) | 1500–2250 | 15 minutes | Preventive disinfection |
| Bacterial spores | 500–30,000 (0.05–3.00%) | 15 minutes/ 15 seconds | High-level disinfection Sterilization |

This simple table shows that owing to the versatility of the system of the present invention (which makes it possible to obtain different concentrations of PAA), the solution can be used for:

1) a primary decontamination of medical-surgical instruments (including endoscopes) also for protection against contamination with HIV in public and private medical facilities, according to statutory provisions in force, at PAA concentrations of 0.2–00 to 0.500% (2000–5000 ppm) for a contact time of 5–30 minutes;

2) high-level disinfection or sterilization of medical and surgical instruments (including endoscopes) at PAA concentrations of 0.200 to 3.00% (2000–30,000 ppm) for contact times of 20 minutes to 30 seconds, respectively.

The present invention also provides for the use of solutions of peracetic acid at different concentrations which are prepared just before use through a physical system for ultrasound generation (sonicator) in order to improve:

their germicidal effectiveness, since by disrupting bacterial colonies and any residues of organic material the surface of contact with the disinfectant solution is increased; and their diffusion and ability to penetrate confined spaces by bursting oxygen bubbles in the solution that would prevent direct contact of the disinfectant solution with some areas of a medical or surgical instrument, which thus remains contaminated.

The above described invention is susceptible of numerous modifications and variations within the scope as defined by the claims.

The disclosures in Italian Patent Application No. VR98A000033 from which this application claims priority are incorporated herein by reference.

What is claimed is:

1. A method for preparation of a synergistic disinfectant peracetic acid hydroalcoholic solution having improved active life and stability, said method comprising reacting an acetylated compound and peroxide compound, wherein at least of the reagents is provided in the form of a hydroalcoholic solution having an acidic pH to provide a synergistic germicidal activity, said peroxide compound is provided in a molar excess to avoid occurrence of hydrolysis phenomena.

2. The method according to claim 1, further comprising a dilution of the peracetic acid based solution with a buffered water based solution to reach a pH in the range of 3.5 to 7.

3. The method according to claim 1, wherein said acetylated compound is selected from the group consisting of N-acetylated compounds, O-acetylated compounds and mixtures thereof.

4. The method according to claim 3, wherein said N-acetylated compounds are selected from the group consisting of N,N,N,N-tetracetyl gycoluryle, tetracetyl ethylene diamine mixtures thereof.

5. The method according to claim 3, wherein said O-acetylated compound is acetic acid.

6. The method according to claim 1, wherein said peroxide compound is selected from the group consisting of hydrogen peroxide, sodium perborate, carbamide peroxide and mixtures thereof.

* * * * *

UNITED STATES PATENT AND TRADEMARK OFFICE
CERTIFICATE OF CORRECTION

PATENT NO.    : 6,514,509 B2
DATED         : February 4, 2003
INVENTOR(S)   : Renato Tabasso It is certified that error appears in the above-identified patent and that said Letters Patent is hereby corrected as shown below:

<u>Column 34,</u>
Line 32, after "at least" and before "of the reagents" please insert -- one --.
Line 47, after "diamine" and before "mixtures" please insert -- and --.

Signed and Sealed this

Twenty-sixth Day of August, 2003

JAMES E. ROGAN
*Director of the United States Patent and Trademark Office*